United States Patent [19]
David et al.

[11] 4,376,110
[45] Mar. 8, 1983

[54] IMMUNOMETRIC ASSAYS USING MONOCLONAL ANTIBODIES

[75] Inventors: Gary S. David, La Jolla; Howard E. Greene, Carlsbad, both of Calif.

[73] Assignee: Hybritech, Incorporated, La Jolla, Calif.

[21] Appl. No.: 175,133

[22] Filed: Aug. 4, 1980

[51] Int. Cl.³ .................. G01N 33/54; G01N 33/56
[52] U.S. Cl. ..................................... 436/513; 435/7; 436/548; 436/529; 436/540
[58] Field of Search .............. 23/230 B; 424/12, 1, 424/8; 435/7

[56] References Cited
U.S. PATENT DOCUMENTS

| 3,654,090 | 4/1972 | Schuurs | 435/7 |
| 3,791,932 | 2/1974 | Schuurs | 435/7 |
| 3,867,517 | 2/1975 | Ling | 23/230 B X |
| 4,016,043 | 4/1977 | Schuurs | 435/7 |
| 4,098,876 | 7/1978 | Piasio | 424/12 X |

OTHER PUBLICATIONS

A. C. Cuello et al., Proc. Natl. Acad. Sci. U.S.A., vol. 76(7), 3532–3536 (Jul. 1979).

Primary Examiner—Sidney Marantz
Attorney, Agent, or Firm—Lyon & Lyon

[57] ABSTRACT

"Two-site" or "sandwich" immunometric assay techniques for determination of the presence and/or concentration of antigenic substances in fluids using monoclonal antibodies. One monoclonal antibody is presented in a soluble labeled form and a second monoclonal antibody is presented bound to a solid carrier; the soluble and bound monoclonal antibodies may be the products of either the same or different cell lines. Each monoclonal antibody has an affinity for the antigenic substances of at least about $10^8$ liters/mole.

29 Claims, 2 Drawing Figures

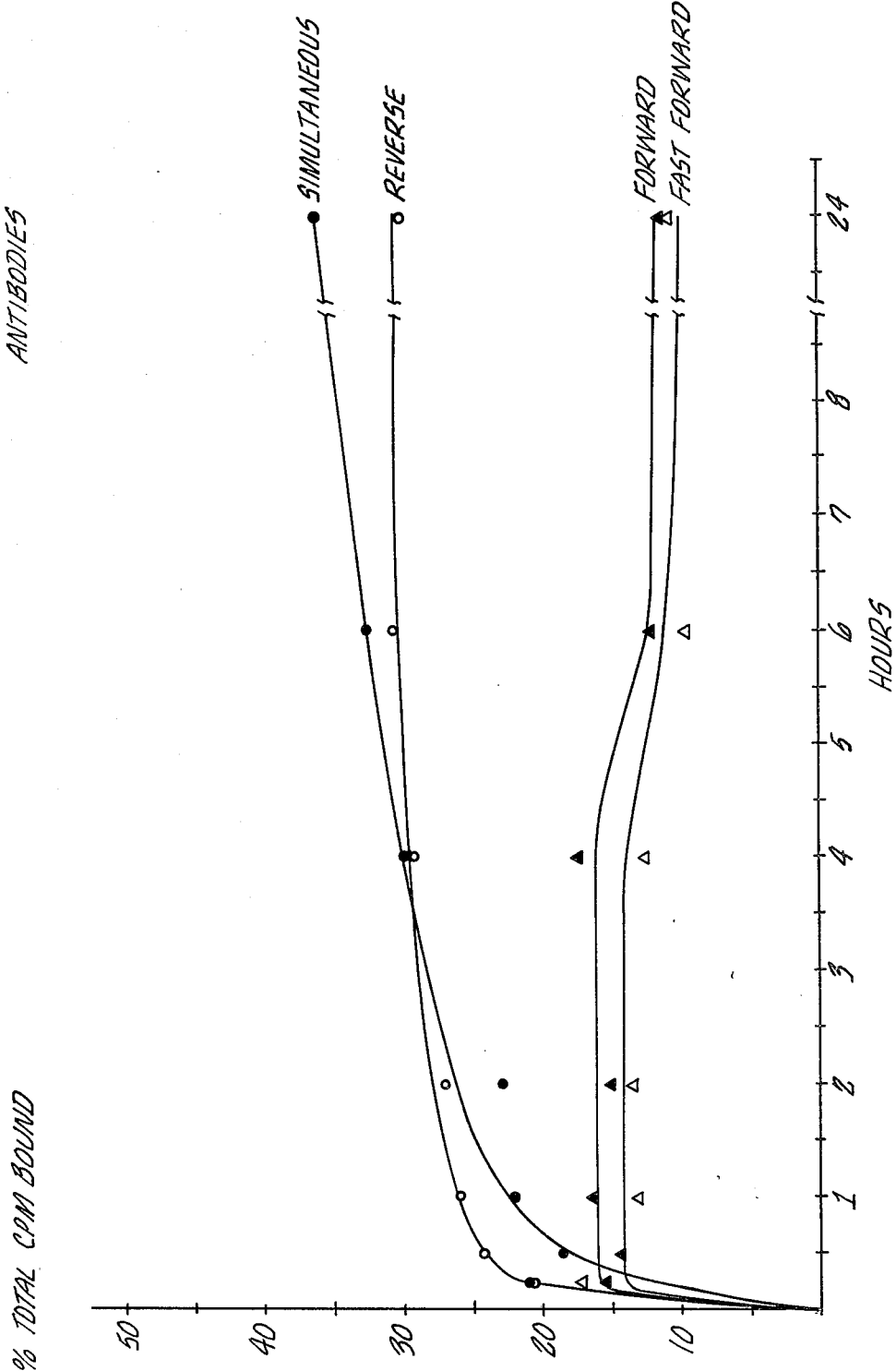

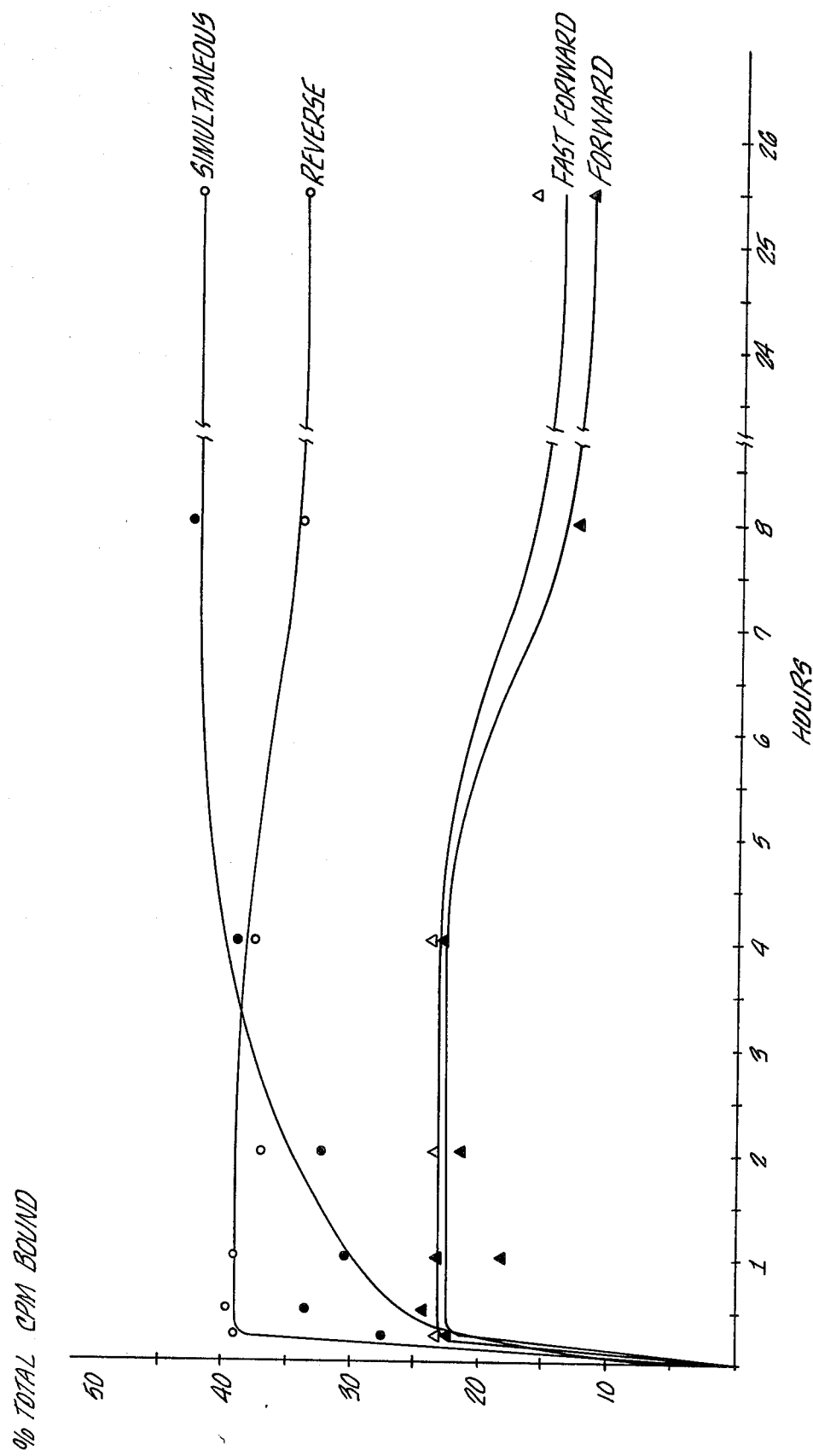

IMMUNOMETRIC ASSAYS USING MONOCLONAL ANTIBODIES

FIELD OF THE INVENTION

This invention relates to methods for detecting and/or determining the concentration of antigenic substances in fluids such as serum. In another aspect it relates to immunometric assay techniques. In yet another aspect it relates to monoclonal antibodies.

BACKGROUND

The determination of the presence or concentration of antigenic substances, for example, those associated with a wide variety of physiological disorders, in serum or other body fluids relies increasingly upon immunoassay techniques. These techniques are based upon formation of a complex between the antigenic substance being assayed and an antibody or antibodies in which one or the other member of the complex may be labelled, for example, by a radioactive element such as $I^{125}$, which permits its detection and/or quantitative analysis after separation of the complexed labelled antigen or antibody from uncomplexed labelled antigen or antibody.

In the case of a competition immunoassay technique, the antigenic substance in a sample of fluid being tested for its presence competes with a known quantity of labelled antigen for a limited quantity of antibody binding sites. Thus, the amount of labelled antigen bound to the antibody is inversely proportional to the amount of antigen in the sample. By contrast, immunometric assays employ a labelled antibody. In such an assay, the amount of labelled antibody associated with the complex is directly proportional to the amount of antigenic substance in the fluid sample.

Immunometric assays have been found to be particularly well suited for the detection of polyvalent antigens, i.e., antigenic substances that are able to complex with two or more antibodies at the same time. Such assays employ a quantity of unlabelled antibody bound to a solid support that is insoluble in the fluid being tested and a quantity of soluble antibody bearing a label such as a radioactive isotope that permits detection and/or a quantitative estimate of the amount of the ternary complex formed between solid phase antibody, antigen, and labelled antibody.

In immunometric assays known to the prior art, typically a "forward" assay, in which the antibody bound to the solid phase is first contacted with the sample being tested to extract the antigen from the sample by formation of a binary solid phase antibody:antigen complex, is employed. After a suitable incubation period, the solid support is washed to remove the residue of the fluid sample, including unreacted antigen if any, and then contacted with a solution containing a known quantity of labelled antibody.

After a second incubation period to permit the labelled antibody to complex with the antigen bound to the solid support through the unlabelled antibody, the solid support is washed a second time to remove the unreacted labelled antibody. In a simple "yes/no" assay to determine whether the antigen is present in the sample being tested, the washed solid support is tested to detect the presence of labelled antibody, for example, by measuring emitted radiation if the label is a radioactive element. The amount of labelled antibody detected is compared to that for a negative control sample known to be free of the antigen. Detection of labelled antibody in amounts substantially above the background levels indicated by the negative control is interpreted to indicate the presence of the suspect antigen. Quantitative determinations can be made by comparing the measure of labelled antibody with that obtained for standard samples containing known quantities of the antigen.

This kind of assay is frequently referred to as a "two-site" or "sandwich" assay since the antigen has two antibodies bonded to its surface at different locations. This and related techniques are described by Wide at pp. 199–206 of "Radiommunoassay Methods", Edited by Kirkham and Hunter, E. & S. Livingstone, Edinburgh, 1970. An assay based on this technique for the detection of the antigen associated with serum hepatitis using an $125_I$ labelled antibody is described in U.S. Pat. No. 3,867,517.

Despite their great utility, the prior art immunometric assays have been recognized to be slow procedures, in part because two washing steps are required and because lengthy incubation periods are required to reach equilibrium, i.e., the point at which the amount of complex formed does not change with increasing time.

To eliminate at least one of the washing steps associated with this procedure, so-called "simultaneous" and "reverse" assays have been proposed. A simultaneous assay involves a single incubation step as the antibody bound to the solid support and the labelled antibody are both added to the sample being tested at the same time. After the incubation is completed, the solid support is washed to remove the residue of fluid sample and uncomplexed labelled antibody. The presence of labelled antibody associated with the solid support is then determined as it would be in a conventional "forward" sandwich assay.

A reverse assay involves the stepwise addition first of a solution of labelled antibody to the fluid sample followed by the addition of unlabelled antibody bound to a solid support after a suitable incubation period. After a second incubation, the solid phase is washed in conventional fashion to free it of the residue of the sample being tested and the solution of unreacted labelled antibody. The determination of labelled antibody associated with the solid support is then determined as in the simultaneous and forward assays.

Both the simultaneous and reverse assay techniques require a sufficient excess amount of solid phase antibody to bind most or all of the antigen present to avoid a high dose hook effect where artificially negative or low quantitation of antigen is observed at extremely high concentrations of antigen. For this reason, the forward assay has been the approach preferred by the prior art. That is because large amounts of highly purified, active antibody specific to the antigen of interest for preparing a solid phase with sufficient antigen binding capacity is difficult to obtain from the "polyclonal" antibodies used in prior art processes. Methods for affinity purifying such antibodies have generally been time consuming and resulted in low yields and loss of high affinity antibodies. When an immunogenic substance is introduced into a living body, the body's immune system reacts by generating antibodies to every site on the immunogen it recognizes. A large immunogenic protein molecule may have dozens of sites and a foreign cell may have hundreds. Thus, while each antibody producing cell produces antibody specific for a single antigenic site the immune system has generated a specie of specific antibody producing cells for each immunogenic site recognized. In addition, the body has produced relatively large quantities of antibodies to antigens other than the one of interest such that most of the antibody in the polyclonal mixture is not specific for the antigen of interest. Accordingly, the antibodies used in prior immunometric assays are necessarily "polyclonal" in nature since the antibodies are derived from antisera raised in a conventional manner in animals and their purification is difficult.

When employing conventional polyclonal antibody mixtures in the reverse and simultaneous assays, the formation of a "sandwich" comprising the antigen complexed by two or more labelled antibodies which complex with the antigen at different sites is possible. These complexes could remain soluble in the sample being tested, be removed by subsequent washing steps, and not "counted" when the solid phase is analyzed for solid phase bound labelled antibody. If this happens to a significant extent, sensitivity of the assay is reduced and erroneous results may arise. However, if the unlabelled bound antibody is added to the sample first as in the forward sandwich assay, steric considerations prevent formation of a sandwich comprising the antigen complexed to two or more unlabelled antibodies where labelled antibody is excluded from also binding to the antigen. Accordingly, the antigen is free to react with a labelled antibody molecule. Nevertheless, it has been proposed to use a simultaneous assay for human thyroid stimulating hormone (HTSH) by employing a large excess of the unlabelled antibody bound to a solid phase to minimize formation by soluble labelled antibodies. See Jeong et al., "Comparison to Radioimmunoassay (RIA) with a Unique, Single-Incubation Two-Site Immunoradiometric Assay (IRMA) as Applied to the Determination of Human Thyroid Stimulating Hormone (HTSH)", Bio-Rad Laboratories, 1979.

It has also been proposed to use a reverse assay for HTSH, hepatitis associated antigen (HAA) and carcinoembryonic antigen (CEA) by employing a quantity of labelled antibody sufficient to assure a labelled antibody:antigen complex but insufficient to form a "sandwich" of all the antigen present in a sample. See U.S. Pat. No. 4,098,876.

Since all three of the procedures known to the prior art use a polyclonal mixture of antibodies, the potential for cross-reaction with other materials in serum or other fluid than the antigen for which the test is intended is increased. The occurrence of cross-reactivity with other antigens also reduces the sensitivity of the test for the suspect antigen and increases the prospect of a "false-positive" assay. Furthermore, the use of polyclonal antibodies in a simultaneous or reverse assay requires a careful consideration of the amount of labelled antibody used relative to the amount of solid phase antibody and/or antigen present.

In view of these shortcomings, the limitations to the immunometric procedures known to the prior art are readily apparent. The conventional forward assay is time consuming; the simultaneous and reverse assays are accomplished with fewer steps but require large quantities of solid-phase specific antibody and are not well suited to determination of small concentrations of antigen since formation of a sandwich of the antigen with a multiple number of labelled antibody molecules competes with formation of the sandwich comprising bound antibody:antigen:labelled antibody; and all are subject to misinterpretation of false-positives due to the polyclonal nature of the antibody.

Accordingly, one object of the present invention is to provide an improved process for the immunometric assay for antigenic substances.

More specifically, an object of the present invention is to provide more rapid immunometric assay techniques.

Another object of the present invention is to provide more sensitive immunometric assay techniques.

Yet another object of the present invention is to provide improved "simultaneous" and "reverse" immunometric assays.

The manner in which these and other objects are realized by the present invention will be apparent from the summary and detailed description set forth below.

SUMMARY OF THE INVENTION

According to the present invention, the polyclonal antibody used in an immunometric assay as the unlabelled antibody bound to a solid support and the antibody used as the soluble labelled antibody are replaced by at least one and usually two or more different monoclonal antibodies, i.e., each antibody specific to a single antigenic site and separately produced by clones derived from unique cell lines. In a preferred embodiment of the invention, the monoclonal antibody used as the antibody bound to the solid support is the product of a different cell line than is the monoclonal antibody used for the labelled antibody and the two monoclonal antibodies are selected to bind the antigenic substance at sites remote from each other so as to not interfere with the others binding to the antigen. The advantages of the present invention, particularly in simultaneous and reverse assays, over prior art methods will become clear after consideration of the accompanying drawings and the following detailed description of the invention.

BRIEF DESCRIPTION OF THE DRAWINGS

FIG. 1 is a graph illustrating the results obtained using polyclonal antibodies in four types of immunometric assay for human IgE.

FIG. 2 is a similar graph illustrating the difference in results obtained using monoclonal antibodies in the same four types of immunometric assay for human IgE.

DETAILED DESCRIPTION OF THE INVENTION

As indicated above, according to the present invention, the polyclonal antibody used in an immunometric assay for an antigenic substance is replaced by a monoclonal antibody. The present invention is useful for the determination of the presence or concentration of a wide variety of polyvalent antigenic substances. Accordingly, as used herein, the term antigen or antigenic substance refers broadly to substances to which antibodies can be produced. Among such substances may be mentioned haptens, hormones such as insulin and human thyroid stimulating hormone (HTSH), gamma globulins, allergens, viruses, virus subunits, bacteria, toxins such as those associated with tetanus and with animal venoms, and even some drugs. Among the specific antigens which may be assayed by the process of the present invention may be mentioned carcinoembryonic antigen (CEA), hepatitis A and B, hepatitis Non A/Non B, IgE and alphafetoprotein.

The monoclonal antibodies useful in the present invention are obtained by the process discussed by Milstein and Kohler and reported in Nature 256 495–497, 1975. The details of this process are well known and will not be repeated here. However, basically it involves injecting a mouse, or other suitable animal, with an immunogen. The mouse is subsequently sacrificed and cells taken from its spleen are fused with myeloma cells. The result is a hybrid cell, referred to as a "hybridoma", that reproduces in vitro. The population of hybridomas are screened to isolate individual clones each of which secrete a single antibody species to the antigen. The individual antibody species obtained in this way are each the product of a single B cell from the immune animal generated in response to a specific antigenic site recognized on the immunogenic substance.

When an immunogenic substance is introduced into a living host, the host's immune system responds by producing antibodies to all the recognizable sites on the substance. This "shotgun" approach to producing antibodies to combat the invader results in the production of antibodies of differing affinities and specificities for the immunogenic substance. Accordingly, after the different hybridoma cell lines are screened to identify those that produce antibody to the desired antigen, the antibodies produced by the individual hybridoma cell lines are preferably screened to identify those having the highest affinity for the immunogenic substance stimulating their original production before selection for use in the present invention. Selection based on this criterion is believed to help provide the increased sensitivity in the immunometric assay of the present invention using monoclonal antibody compared to the polyclonal antibody used in the prior art which, at best, has an affinity for the antigen which is roughly the average of the affinities of all antibodies produced by the immune system. Preferably, the monoclonal antibody selected will have an affinity of at least $10^8$ liters/mole and, more preferably, an affinity of at least about $10^9$ liters/mole.

Furthermore, those monoclonal antibodies having the highest affinities can be further screened by running a simulated assay on specimens known to give false positive results with processes employing conventional polyclonal antibodies to identify those monoclonal antibodies which do not cross-react and give false positive results.

Because the two-site immunometric assay relies upon formation of an antibody:antigen:antibody sandwich, usually two different monoclonal antibodies which do not interfere with the binding of each other to the antigen are selected to be the bound antibody and the soluble labelled antibody. Since both are necessary to complete the sandwich, reverse and simultaneous assays can be conducted without concern that a complex of labelled antibody:antigen:labelled antibody will form which will preclude formation of a complex between the antigen and the antibody bound to the solid phase and therein lies a particular advantage of the present invention. Furthermore, a forward assay can be accomplished without the intermediate washing step since the two antibodies bind to different sites. We refer to such a process as a "fast forward" assay.

However, particularly in the case of a forward assay, the same monoclonal antibody can be used for both the labelled antibody and the antibody bound to the solid support when the antigenic substance possesses identical antibody binding sites sufficiently remote from each other to allow more than one antibody molecule to be bound at the same time. In such a system the addition first of the bound antibody to the sample precludes formation of a sandwich because of steric considerations. When the labelled monoclonal antibody is subsequently added, it is also able to complex with the antigen bound to unlabelled antibody on the solid phase.

The unlabelled monoclonal antibody used in the presence of the present invention to extract the antigenic substance from the sample being tested may be immobilized on any of the common supports used in immunometric assays. Among these may be mentioned filter paper, plastic beads or test tubes made from polyethylene, polystyrene, polypropylene or other suitable material. Also useful are particulate materials such as agarose, crosslinked dextran, and other polysaccharides. The techniques for such bonding are well known to those skilled in the art. For example, antibodies may be bound to polysaccharide polymers using the process described in U.S. Pat. No. 3,645,852.

The labelled monoclonal antibody used in the present invention may be provided with the same labels used in prior art immunometric assays. Among these may be mentioned fluorogenic labels for detection by fluorimetry as described in U.S. Pat. No. 3,940,475 and enzymatic markers as described in U.S. Pat. No. 3,645,090. It is presently preferred to label the antibody with a radioisotope such as $I^{125}$ using, for example, the procedure of Hunter and Greenwood, *Nature*, 144 (1962), page 945 or that of David et al., *Biochemistry*, Vol. 13, pp. 1014–1021, 1974.

In a typical assay, the amount of labelled antibody associated with the insoluble sandwich complex is determined by examination of the insoluble carrier material by suitable means. However, it is also possible to relate the presence or absence of antigen in the fluid sample being assayed to the amount of labelled antibody which does not react during the assay and remains in a soluble form.

The advantages of the present invention in which monoclonal antibodies are used in immunometric assays as compared to polyclonal antibodies are seen by reference to the following example. In this example, four comparative assays, a simultaneous assay, a reverse assay, a forward assay, and a "fast" forward assay, were run using both monoclonal antibody and polyclonal antibody using a standard serum containing 100 IU/ml of human IgE as the positive sample. Normal horse serum containing no IgE was used as a negative control.

The polyclonal antibody to IgE used, as the labelled antibody in the example was obtained from Pharmacia Diagnostics of Piscataway, New Jersey. The polyclonal antibody bound to the solid support was obtained from Tago, Inc. of Burlingame, California.

Monoclonal antibody to IgE was obtained using the method of Milstein and Kohler discussed above. The two antibodies selected each exhibited an affinity for IgE of greater than $10^9$ liters/mole and did not interfere with the others binding to IgE.

The assays were run using unlabelled antibody bound to agarose by the process of U.S. Pat. No. 3,645,852. Labelling of antibody was by $125_I$ according to the process of David et al. referred to above. Phosphate buffered saline, pH 7.4, was used to wash all samples.

EXAMPLE (1) Simultaneous Assay Method

Duplicate samples were run in which 100 μl of a suspension of antibody immobilized on agarose particles is mixed with 100 μl of specimen (serum) and 100 μl of soluble $^{125}$I-labelled antibody. This mixture as incubated for the specified times shown in Table I (for polyclonal antibody) and Table II (for monoclonal antibody) set forth below, plus 30 minutes. The extra 30 minutes incubation period was added to equalize this assay method with the other assay methods which required an additional 30 minute incubation time for a second added reagent. Following the incubation periods the agarose particles were washed by addition of buffer and centrifuged. After removal of the washing liquid by aspiration, the resulting pellet of agarose particles was then counted for bound $^{125}$I-labelled antibody. The counts obtained for each of the complexes after the specified incubation time are set forth in Tables I and II.

(2) Reverse Assay Method

Duplicate samples were run in which 100 μl of specimen (serum) is mixed with 100 μl of $^{125}$I-labelled soluble antibody and incubated for the specified times shown in Tables I and II. 100 μl of a suspension of antibody immobilized on agarose particles is then added and the mixture was allowed to incubate for another 30 minutes. The agarose particles were then washed and counted as in the simultaneous assay method. The counts are reported in Tables I and II.

(3) Forward Assay Method

Duplicate samples were run in which 100 μl of specimen (serum) is mixed with 100 μl of a suspension of antibody immobilized on agarose particles and incubated for the specified times shown in Tables I and II. The agarose particles were then washed once by the addition of 2.5–3.0 ml of buffer which, after mixing, was centrifuged, and the liquid removed by aspiration. 100 μl of $^{125}$I-labelled soluble antibody was then added and the mixture incubated an additional 30 minutes. The agarose particles were then washed and counted as in the simultaneous assay method. The counts were reported in Tables I and II.

(4) Fast Forward Assay Method

The assay was performed, in duplicate, in a similar manner to the forward assay method except that the wash step between the initial incubation of specimen with antibody immobilized on agarose particles and the addition of soluble $^{125}$I-labelled antibody was omitted.

The counts/minute for the duplicate controls and the duplicate assays of the samples containing IgE using polyclonal antibody and monoclonal antibody are shown in Tables I and II, respectively. These data were used to prepare FIGS. I and II in the following way: The average of the counts/minute for a control for a given incubation period was subtracted from the average of the counts for the corresponding IgE assay. The difference was calculated as a percentage of the total counts/minute of labelled antibody added to the sample and is plotted on the Y axis as the percentage of total counts/minute of antibody bound to the solid phase. The incubation time is plotted on the X axis.

A comparison of the plots shown in FIG. 2 displaying the results of assays using monoclonal antibody with those of FIG. 1 of assays using polyclonal antibody shows that in each kind of assay, simultaneous, reverse, forward, and fast forward, the assay using monoclonal antibody was more sensitive as indicated by the higher percentage of total counts bound to the solid phase with 100 IU IgE/ml specimen. Unexpectedly, in the case of the simultaneous and reverse assays, we have found that those run with monoclonal antibody reach eqilibrium more rapidly than does the corresponding assay using polyclonal antibody. Therefore, by using a monoclonal antibody in these procedures, the time for the assay can be reduced significantly beyond the time saving achieved by merely eliminating a washing step. In that regard, the reverse assay with monoclonal antibody reached equilibrium in less than one hour. The same assay run with polyclonal assay did not reach equilibrium until after 4 hours. Similarly, in the case of simultaneous assays, the assay using monoclonal antibody reached equilibrium within 8 hours whereas the assay with polyclonal antibody did not reach equilibrium within 24 hours. Accordingly, the present invention substantially provides more rapid and sensitive simultaneous and reverse assays than the prior art processes and eliminates the concern that formation of a soluble "sandwich" complex will compete with formation of the desired insoluble complex.

The examples described above using monoclonal antibody to assay for IgE is merely one exemplar of the use of the present invention. That variations in the actual processes described in the example will be useful will be apparent to those skilled in the art. Therefore, the present invention is to be considered limited only by the appended claims.

TABLE I

| | Assay Results Using Polyclonal Antibody | | | | | | | |
|---|---|---|---|---|---|---|---|---|
| | Simultaneous Assay | | Reverse Assay | | Forward Assay | | Fast Forward Assay | |
| Incubation Time (Hrs) | Control Samples | IgE Samples | Control Samples | IgE Samples | Control Samples | IgE Samples | Control Samples | IgE Samples |
| 0.25 | 372,314 | 2705,2667 | 302,243 | 2568,2581 | 357,326 | 2092,2077 | 396,293 | 2271,2238 |
| 0.50 | 348,265 | 2391,2366 | 284,262 | 2958,2999 | 288,233 | 1905,1817 | —,— | —,— |
| 1.00 | 315,277 | 2793,2708 | 305,277 | 3154,3218 | 355,424 | 2157,2255 | 304,284 | 1789,1706 |
| 2.00 | 342,356 | 2897,2887 | 290,274 | 3377,3212 | 302,314 | 1946,2019 | 288,312 | 1728,1867 |
| 4.00 | 421,385 | 3696,3746 | 28,280 | 3413,3651 | 274,255 | 2019,2392 | 283,292 | 1720,1683 |
| 6.00 | 447,436 | 4028,4101 | 296,281 | 3762,3643 | 241,267 | 1750,1452 | 301,257 | 1283,1424 |
| 24.00 | 526,577 | 4564,4628 | 233,263 | 3651,3546 | 320,277 | 1553,1604 | 273,256 | 1450,1470 |

TABLE II

| | Assay Results Using Monoclonal Antibody | | | | | | | |
|---|---|---|---|---|---|---|---|---|
| | Simultaneous Assay | | Reverse Assay | | Forward Assay | | Fast Forward Assay | |
| Incubation Time (Hrs) | Control Samples | IgE Samples | Control Samples | IgE Samples | Control Samples | IgE Samples | Control Samples | IgE Samples |
| 0.25 | 135,132 | 5610,5803 | 388,594 | 8407,8358 | 210,205 | 4618,4894 | 194,183 | 4859,4906 |
| 0.50 | 558,459 | 7472,7115 | 240,231 | 8238,8271 | 223,228 | 4987,5273 | 198,197 | 5024,5152 |
| 1.00 | 268,265 | 6289,6529 | 325,265 | 8010,8377 | 230,187 | 3454,4308 | 215,192 | 4887,4901 |

TABLE II-continued

| | Assay Results Using Monoclonal Antibody | | | | | | | |
|---|---|---|---|---|---|---|---|---|
| | Simultaneous Assay | | Reverse Assay | | Forward Assay | | Fast Forward Assay | |
| Incubation Time (Hrs) | Control Samples | IgE Samples | Control Samples | IgE Samples | Control Samples | IgE Samples | Control Samples | IgE Samples |
| 2.00 | 282,275 | 6787,6784 | 255,302 | 7856,7644 | 226,197 | 4834,4268 | 192,210 | 4937,4944 |
| 4.00 | 308,272 | 8150,8155 | 343,305 | 8017,7788 | 231,216 | 5269,4420 | 218,187 | 4929,5071 |
| 8.00 | 549,667 | 8884,9494 | 698,850 | 7870,7358 | 226,361 | 2006,3631 | 405,243 | 3033,3713 |
| 25.55 | 426,420 | 8669,9044 | 497,323 | 7037,7359 | 194,201 | 2465,2586 | 246,233 | 3945,2943 |

We claim:

1. A process for the determination of the presence of concentration of an antigenic substance in a fluid comprising the steps:
   (a) contacting a sample of the fluid with a measured amount of a soluble first monoclonal antibody to the antigenic substance in order to form a soluble complex of the antibody and antigenic substance present in said sample, said first monoclonal antibody being labelled;
   (b) contacting the soluble complex with a second monoclonal antibody to the antigenic substance, said second monoclonal antibody being bound to a solid carrier, said solid carrier being insoluble in said fluid, in order to form an insoluble complex of said first monoclonal antibody, said antigenic substance and said second monoclonal antibody bound to said solid carrier;
   (c) separating said solid carrier from the fluid sample and unreacted labelled antibody;
   (d) measuring either the amount of labelled antibody associated with the solid carrier or the amount of unreacted labelled antibody; and
   (e) relating the amount of labelled antibody measured with the amount of labelled antibody measured for a control sample prepared in accordance with steps (a)-(d), said control sample being known to be free of said antigenic substance, to determine the presence of antigenic substance in said fluid sample, or relating the amount of labelled antibody measured with the amount of labelled antibody measured for samples containing known amounts of antigenic substance prepared in accordance with steps (a)-(d) to determine the concentration of antigenic substance in said fluid sample, the first and second monoclonal antibodies having an affinity for the antigenic substance of at least about $10^8$ liters/mole.

2. A process according to claim 1 wherein said first monoclonal antibody is the product of a different cell line than said second monoclonal antibody.

3. A process according to claim 1 wherein said antigen has at least two identical binding sites and said first and second monoclonal antibodies are the product of the same cell line.

4. A process according to claims 1, 2 or 3 wherein the affinity is at least about $10^9$ liters/mole.

5. A process according to any of claims 1, 2 or 3 wherein said solid carrier resulting from step (d) is washed to separate the fluid sample from the carrier.

6. A process according to claim 5 wherein the solid carrier is washed with phosphate buffered saline.

7. A process according to claims 1, 2 or 3 wherein the antigenic substance is selected from the group consisting of IgE, hepatitis A, hepatitis B, hepatitis Non A/Non B, alphafetoprotein, carcinoembryonic antigen, insulin and human thyroid stimulating hormone.

8. A process according to claims 1, 2 or 3 wherein the labelled antibody is labelled with a member selected from the group consisting of a radioactive isotope, an enzyme and a fluorogenic material and said examination is by means selected from the group consisting of radiometric means, enzymatic means and fluorometric means.

9. A process according to claim 8 wherein said label is the radioactive isotope $^{125}$I.

10. A process for the determination of the presence of an antigenic substance in a fluid comprising the steps:
    (a) simultaneously contacting a sample of the fluid with first and second monoclonal antibodies to said antigenic substance, each monoclonal antibody having an affinity for the antigenic substance of at least about $10^8$ liters/mole, said first monoclonal antibody being labelled and soluble in said fluid and being provided for in a measured amount and said second monoclonal antibody being bound to a solid carrier insoluble in said fluid, in order to form an insoluble complex of said first monoclonal antibody, said antigenic substance and said second antibody;
    (b) separating said solid carrier from the fluid sample and unreacted labelled antibody;
    (c) measuring either the amount of labelled antibody associated with the solid carrier or the amount of unreacted labelled antibody; and
    (d) relating the amount of labelled antibody measured with the amount of labelled antibody measured for a control sample prepared in accordance with steps (a)-(c), said control sample being known to be free of said antigenic substance, to determine the presence of antigenic substance in said fluid sample, or relating the amount of labelled antibody measured with the amount of labelled antibody measured for samples containing known amounts of antigenic substance prepared in accordance with steps (a)-(d) to determine the concentration of antigenic substance in said fluid sample.

11. A process according to claim 10 wherein said first monoclonal antibody is the product of a different cell line than said second monoclonal antibody.

12. A process according to claim 10 wherein said antigenic substance has at least two identical binding sites and said first and second monoclonal antibodies are the product of the same cell line.

13. A process according to claims 10, 11 or 12 wherein the affinity is at least about $10^9$ liters/mole.

14. A process according to any of claims 10, 11 or 12 wherein said solid carrier resulting from step (b) is washed to separate the fluid sample from the carrier.

15. A process according to claim 14 wherein the solid carrier is washed with phosphate buffered saline.

16. A process according to claims 10, 11 or 12 wherein the antigenic substance is selected from the group consisting of IgE, hepatitis A, hepatitis B, hepatitis Non A/Non B, alphafetoprotein, carcinoembryonic antigen, insulin and human thyroid stimulating hormone.

17. A process according to claims 10, 11 or 12 wherein the labelled antibody is labelled with a member selected from the group consisting of a radioactive isotope, an enzyme and a fluorogenic material and said examination is by means selected from the group consisting of radiometric means, enzymatic means and fluorometric means.

18. A process according to claim 17 wherein said label is the radioactive isotope $^{125}I$.

19. In an immunometric assay to determine the presence or concentration of an antigenic substance in a sample of a fluid comprising forming a ternary complex of a first labelled antibody, said antigenic substance, and a second antibody said second antibody being bound to a solid carrier insoluble in said fluid wherein the presence of the antigenic substance in the samples is determined by measuring either the amount of labelled antibody bound to the solid carrier or the amount of unreacted labelled antibody, the improvement comprising employing monoclonal antibodies having an affinity for the antigenic substance of at least about $10^8$ liters/mole for each of said labelled antibody and said antibody bound to a solid carrier.

20. A process according to claim 19 wherein the fluid sample is first contacted with the second monoclonal antibody to form a binary complex of the antigenic substance and said second monoclonal antibody insoluble in the fluid and then contacted with said first labelled monoclonal antibody to form the ternary complex.

21. A process according to claim 19 wherein the fluid sample is first contacted with the second monoclonal antibody to form a binary complex of the antigenic substance and said second monoclonal antibody insoluble in the fluid; the sample separated from the solid carrier and the solid carrier contacted with a solution of said first labelled monoclonal antibody to form said ternary complex.

22. A process according to claim 21 wherein said solid carrier after formation of the ternary complex is washed to separate the fluid sample from the carrier.

23. A process according to claim 22 wherein the solid carrier is washed with phosphate buffered saline.

24. A process according to claims 19, 20 or 21 wherein said first monoclonal antibody is the product of a different cell line than said second monoclonal antibody.

25. A process according to claims 19, 20 or 21 wherein said antigen has at least two identical binding sites and said first and second monoclonal antibodies are the product of the same cell line.

26. A process according to claims 19, 20 or 21 wherein the affinity is at least about $10^9$ liters/mole.

27. A process according to claims 19, 20 or 21 wherein the antigen is selected from the group consisting of IgE, hepatitis A, hepatitis B, hepatitis None A/Non B, alphafetoprotein, carcinoembryonic antigen, insulin and human thyroid stimulating hormone.

28. A process according to claims 19, 20 or 21 wherein the labelled antibody is labelled with a member selected from the group consisting of a radioactive isotope, an enzyme and a fluorogenic material.

29. A process according to claim 28 wherein said label is the radioactive isotope $^{125}I$.

* * * * *

UNITED STATES PATENT AND TRADEMARK OFFICE
CERTIFICATE OF CORRECTION

PATENT NO. : 4,376,110

DATED : March 8, 1983

INVENTOR(S) : GARY S. DAVID and HOWARD E. GREENE

It is certified that error appears in the above-identified patent and that said Letters Patent is hereby corrected as shown below:

Claim 1, line 1 (Column 9, line 15 of the patent), after the word "presence" delete "of" (second occurrence) and substitute -- or --.

Signed and Sealed this

Eighteenth Day of February 1986

[SEAL]

Attest:

Attesting Officer

DONALD J. QUIGG

Commissioner of Patents and Trademarks